US00PP16020P3

(12) United States Plant Patent
van der Voort

(10) Patent No.: US PP16,020 P3
(45) Date of Patent: Oct. 4, 2005

(54) LILY PLANT NAMED 'MANISSA'

(50) Latin Name: ***Lilium L.* hybrid (*oriental×aurelian*)**
Varietal Denomination: Manissa

(75) Inventor: Cees A. van der Voort, Katwijk (NL)

(73) Assignee: Vletter & Den Haan Beheer B..V., Katwijk (NL)

( * ) Notice: Subject to any disclaimer, the term of this patent is extended or adjusted under 35 U.S.C. 154(b) by 0 days.

(21) Appl. No.: 10/607,271

(22) Filed: Jun. 27, 2003

(65) Prior Publication Data

US 2004/0123357 P1 Jun. 24, 2004

Related U.S. Application Data

(60) Provisional application No. 60/392,042, filed on Jun. 28, 2002.

(51) Int. Cl.[7] ..... A01H 5/00

(52) U.S. Cl. ..... Plt./313

(58) Field of Search ..... Plt./313, 315

(56) References Cited

FOREIGN PATENT DOCUMENTS

| | | |
|---|---|---|
| AU | 2427 | 3/2004 |
| NZ | 2126 | 8/2003 |
| PL | 0 1899 | 2/2004 |
| QZ | 10614 | 2/2003 |
| ZA | 20032850 | 3/2003 |

OTHER PUBLICATIONS

UPOV–Rom GTI Jouve Retrieval software, Plant Variety Database 2004/02.*

* cited by examiner

*Primary Examiner*—Anne Marie Grunberg
(74) *Attorney, Agent, or Firm*—Foley & Lardner, LLP

(57) ABSTRACT

A new and distinct cultivar of Lily plant named 'Manissa' characterized by its large, white flowers with bright yellow center color and contrasting orange pollen, and vigorous growth.

1 Drawing Sheet

Latin name of the genus and species of the plant claimed: *Lilium L.* hybrid (*oriental×aurelian*).
Variety denomination: Manissa.

BACKGROUND OF THE INVENTION

This application is based on U.S. provisional Plant patent application Ser. No. 60/392,042, filed Jun. 28, 2002.

The present invention comprises a new and distinct cultivar of lily plant, botanically known as *Lilium L.* (*oriental×aurelian*), and hereinafter referred to by the cultivar name 'Manissa'.

'Manissa' is a product of a planned breeding program which had the objective of creating new lily cultivars having many large, upright flowers and vigorous growth habit.

'Manissa' originated from a hybridization made by the inventor, Cees A. van der Voort, in a controlled breeding program in Rijnsburg, the Netherlands in October, 1997. Both the female and male parents are unnamed proprietary *Lilium L.* seedlings.

'Manissa' was discovered and selected as one flowering plant within the progeny of the stated cross by the inventor in October, 1997 in a controlled environment in Rijnsburg, the Netherlands.

The first act of asexual reproduction of 'Manissa' was accomplished when scales were taken from the initial selection and grown to maturity in a controlled environment in Rijnsburg, the Netherlands by, or under the supervision of, Cees A. van der Voort. Horticultural examination of selected plants has demonstrated that the combination of characteristics as herein disclosed for 'Manissa' are firmly fixed and are retained through successive generations of asexual reproduction.

BRIEF DESCRIPTION OF THE INVENTION

The following traits have been repeatedly observed and are determined to be basic characteristics of 'Manissa' which in combination distinguish this lily as a new and distinct cultivar:

1. large, white flowers with bright yellow center color and contrasting orange pollen; and
2. vigorous growth habit.

Of the many commercial cultivars known to the present inventor, the most similar in comparison to 'Manissa' is the Lily cultivar 'Conca D'or', described in pending U.S. Plant patent application Ser. No. 10/607,304. However, in side-by-side comparisons conducted by the inventor in Stige, Denmark, the main distinction between the two cultivars is:

1. Both plants of 'Manissa' and 'Conca D'or' have a yellow centered flower color with white edges, but 'Manissa' has few buds than 'Conca D'or'.

'Manissa' has not been observed under all possible environmental conditions. The phenotype of the new cultivar may vary significantly with variations in environment such as temperature, light intensity, and daylength without any change in genotype.

BRIEF DESCRIPTION OF THE DRAWING

The accompanying color photographic drawing shows a close-up view of a typical plant of 'Manissa', with colors being as true as possible with illustrations of this type.

The photographic drawing shows the large, white flowers with bright yellow center color and contrasting orange pollen, the buds, and leaves of 'Manissa'.

DETAILED BOTANICAL DESCRIPTION

The following observations, measurements and values describe the new cultivar as grown in Rijnsburg, The Netherlands under conditions which closely approximate those generally used in commercial practice. The plant is grown under controlled climate conditions, preferably in greenhouse constructions. Color references are made to The Royal Horticultural Society (R.H.S.) Colour Chart (publication date 2001), except where general colors of ordinary significance are used. Color values were taken under daylight conditions at approximately 12.00 p.m. in Rijnsburg, The Netherlands. The age of the plant described is about 90 days.

Parentage:

*Male parent.*—Unnamed proprietary seedling (unpatented).

*Female parent.*—Unnamed proprietary seedling (unpatented).

Propagation: Scales were taken from the bulbs.

Plant:

*General appearance and form.*—Height: Tall, 125 cm, depending on growing conditions. Flowering Season: All year round in controlled climate conditions, in a greenhouse.

*Winter hardiness/weather tolerance.*—None.

*Lastingness of the individual bloom.*—Minimum 21 days, depending on storing conditions.

*Rooting habit.*—Vigorous.

*Fragrance.*—Present.

Stem description:

*Length.*—Long, 110 cm., depending growing conditions.

*Diameter.*—3 mm.

*Strength.*—Strong.

Foliage:

*Overall shape of leaf.*—Ovate.

*Quantity.*—Approximately 50–60, depending on growing conditions.

*Length.*—Medium to long, 12 cm, depending on growing conditions.

*Width.*—Medium to wide, 2.5–3 cm, depending on growing conditions.

*Texture.*—Minimal pubescence.

*Color of upper surface.*—Mature leaf: Dark green — RHS 136A. Immature leaf: Dark green — RHS 136B.

*Color of lower surface.*—Mature leaf: Dark green — RHS 136A. Immature leaf: Dark green — RHS 136B.

*Venation color.*—Upper surface: Medium green — RHS 136C. Lower surface: Medium green — RHS 136C.

*Petiole.*—

*Length.*—3 mm. Color: Green — RHS 136C.

Flowers:

*Flower type and habit.*—Raceme.

*Flower size.*—Diameter — 13 cm.

*Overall shape.*—Generally hexagonal star in form and bowl-shaped in cross-section.

*Average number of flowers per lateral branch.*—3, depending on growing conditions.

*Tepals.*—Number of tepals: 6. Texture: Papillose. Tepal size: Long, 8 cm in length; medium to wide, 4 cm in width. Tepal Color: Upper surface: Yellow RHS 12A, RHS 11D at the top. Lower surface: Yellow RHS 12D, RHS 11D at the top.

Bud:

*Form.*—Tapering.

*Color.*—Green — RHS 143C.

*Length.*—7 cm, depending on growing conditions.

*Diameter.*—2.5 cm depending on growing conditions.

*Peduncles.*—5 cm length, angle upright to horizontal, color: medium green — RHS 138A.

Reproductive organs:

*Stamen.*—Number: 6. Color: Yellowish green RHS 145C.

*Seeds.*—None.

*Fruit.*—None.

*Anthers.*—Number: 6. Color: Yellow-Green — RHS 145C.

*Pollen.*—Color: Greyed purple RHS 183B.

*Stigma.*—Quantity: 1. Color: Greyed-orange — RHS 177A.

Disease resistance: No known information.

I claim:

1. A new and distinct cultivar of lily plant named 'Manissa', as illustrated and described herein.

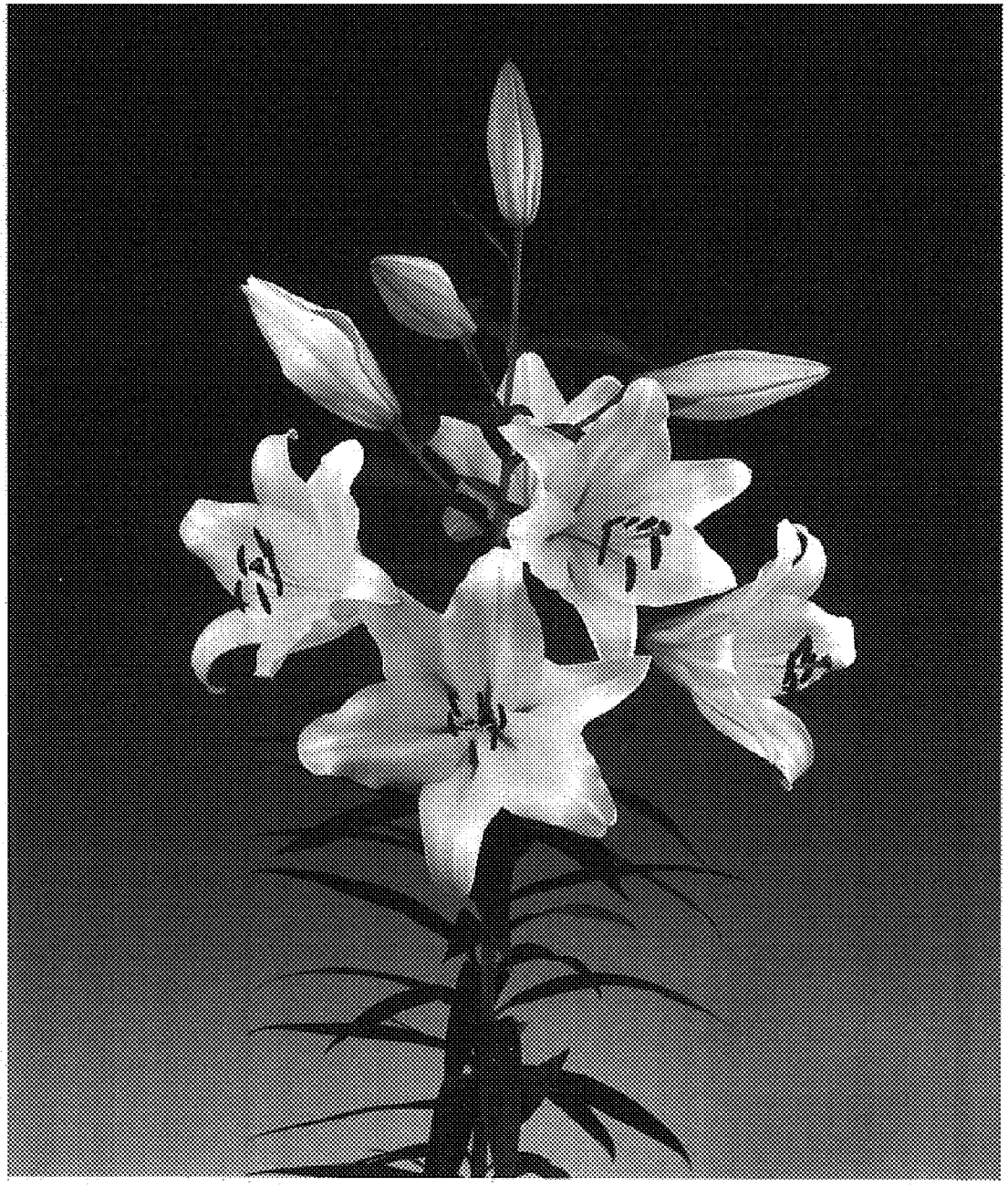

* * * * *